United States Patent
Chopra et al.

(10) Patent No.: US 8,911,543 B2
(45) Date of Patent: Dec. 16, 2014

(54) PHENYLCYCLOHEXANOL DERIVATIVES AS WAX MODIFIERS AND GELATORS

(71) Applicant: Xerox Corporation, Norwalk, CT (US)

(72) Inventors: Naveen Chopra, Oakville (CA); Guerino G. Sacripante, Oakville (CA); Jordan H. Wosnick, Toronto (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/718,338

(22) Filed: Dec. 18, 2012

(65) Prior Publication Data

US 2014/0165873 A1 Jun. 19, 2014

(51) Int. Cl.
C09D 11/02 (2014.01)
C07C 35/21 (2006.01)
C09D 11/34 (2014.01)
C09D 11/00 (2014.01)

(52) U.S. Cl.
CPC ............ *C07C 35/21* (2013.01); *C09D 11/34* (2013.01); *C09D 11/00* (2013.01); *C07C 2101/14* (2013.01)
USPC .................................. 106/31.29; 106/31.61

(58) Field of Classification Search
USPC ........................... 106/31.29, 31.61
See application file for complete search history.

(56) References Cited

U.S. PATENT DOCUMENTS

| | | | |
|---|---|---|---|
| 4,490,731 A | 12/1984 | Vaught | |
| 4,889,560 A | 12/1989 | Jaeger et al. | |
| 4,889,761 A | 12/1989 | Titterington et al. | |
| 5,195,430 A | 3/1993 | Rise | |
| 5,221,335 A | 6/1993 | Williams et al. | |
| 5,372,852 A | 12/1994 | Titterington et al. | |
| 5,389,958 A | 2/1995 | Bui et al. | |
| 5,621,022 A | 4/1997 | Jaeger et al. | |
| 5,688,440 A * | 11/1997 | Garner .......................... | 516/104 |
| 5,750,604 A | 5/1998 | Banning et al. | |
| 5,780,528 A | 7/1998 | Titterington et al. | |
| 5,782,966 A | 7/1998 | Bui et al. | |
| 5,783,658 A | 7/1998 | Banning et al. | |
| 5,827,198 A | 10/1998 | Kassal | |
| 5,830,942 A | 11/1998 | King et al. | |
| 5,876,631 A | 3/1999 | Garner | |
| 5,919,839 A | 7/1999 | Titterington et al. | |
| 5,989,325 A * | 11/1999 | Sacripante et al. ........ | 106/31.27 |
| 6,255,432 B1 | 7/2001 | Evans et al. | |
| 6,309,453 B1 | 10/2001 | Banning et al. | |
| 6,547,380 B2 | 4/2003 | Smith et al. | |
| 6,795,228 B2 | 9/2004 | Sacripante et al. | |
| 6,858,070 B1 | 2/2005 | Wong et al. | |
| 6,860,930 B2 | 3/2005 | Wu et al. | |
| 7,955,429 B2 | 6/2011 | Pozarnsky | |
| 8,287,632 B1 | 10/2012 | Morimitsu et al. | |
| 8,372,189 B2 | 2/2013 | Chopra et al. | |
| 2009/0209776 A1 * | 8/2009 | Pozarnsky ................... | 554/230 |

FOREIGN PATENT DOCUMENTS

| | | |
|---|---|---|
| GB | 2238792 | 6/1991 |
| GB | 2290793 | 1/1996 |
| GB | 2294939 | 5/1996 |
| GB | 2305670 | 4/1997 |
| GB | 2305928 | 4/1997 |
| WO | WO 94/14902 | 7/1994 |
| WO | WO 95/04760 | 2/1995 |
| WO | WO 96/14364 | 5/1996 |
| WO | WO 97/12003 | 4/1997 |
| WO | WO 97/13816 | 4/1997 |
| WO | WO 97/33943 | 9/1997 |

OTHER PUBLICATIONS

Dropping Point, Wikipedia, last modified on Mar. 11, 2013, 2 pages.
Orivone Technical DataSheet, Rev. 2.0 of Mar. 6, 2009, 1 page.

* cited by examiner

*Primary Examiner* — Veronica F Faison
(74) *Attorney, Agent, or Firm* — Marylou J. Lavoie

(57) ABSTRACT

A compound of the formula

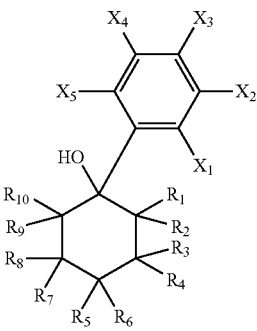

wherein $R_1$, $R_2$, $R_3$, $R_4$, $R_5$, $R_6$, $R_7$, $R_8$, $R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof; wherein $X_1$, $X_2$, $X_3$, $X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can optionally be a mixture of cis and trans isomers wherein only one of $R_1$ to $R_{10}$ is a non-hydrogen group.

8 Claims, No Drawings

PHENYLCYCLOHEXANOL DERIVATIVES AS WAX MODIFIERS AND GELATORS

BACKGROUND

In general, phase change inks (sometimes referred to as solid inks or "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. Nos. 4,889,560, 4,889,761, and 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes.

The colorants can also include pigments, as disclosed in, for example, U.S. Pat. No. 5,221,335, the disclosure of which is totally incorporated herein by reference.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Ink jetting devices are known in the art, and thus extensive description of such devices is not required herein. As described in U.S. Pat. No. 6,547,380, which is hereby incorporated herein by reference in its entirety, ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

In a typical design of a piezoelectric ink jet device utilizing phase change inks printing directly on a substrate or on an intermediate transfer member, such as the one described in U.S. Pat. No. 5,372,852, which is hereby incorporated herein by reference in its entirety, the image is applied by jetting appropriately colored inks during four to eighteen rotations (incremental movements) of a substrate (an image receiving member or intermediate transfer member) with respect to the ink jetting head, i.e., there is a small translation of the print head with respect to the substrate in between each rotation. This approach simplifies the print head design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

As noted, ink jet printing processes may employ inks that are solid at room temperature and liquid at elevated temperatures. For example, U.S. Pat. No. 4,490,731, which is hereby incorporated by reference herein, discloses an apparatus for dispensing solid ink for printing on a substrate such as paper. In thermal ink jet printing processes employing hot melt inks, the solid ink is melted by the heater in the printing apparatus and utilized (i.e., jetted) as a liquid in a manner similar to that of conventional thermal ink jet printing. Upon contact with the printing substrate, the molten ink solidifies rapidly, enabling the colorant to substantially remain on the surface of the substrate instead of being carried into the substrate (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of non-printing without the danger of nozzle clogging, even without capping the nozzles.

Phase change inks can include an ink vehicle that is solid at temperatures of about 23° C. to about 27° C., for example room temperature, and specifically are solid at temperatures below about 60° C. However, the inks change phase upon heating, and are in a molten state at jetting temperatures. Thus, the inks have a viscosity of from about 1 to about 20 centipoise (cps), for example from about 5 to about 15 cps or from about 8 to about 12 cps, at an elevated temperature suitable for ink jet printing, for example temperatures of from about 60° C. to about 150° C.

In this regard, the inks herein may be either low energy inks or high energy inks. Low energy inks are solid at a temperature below about 40° C. and have a viscosity of from about 1 to about 20 centipoise (cps) such as from about 5 to about 15 cps, for example from about 8 to about 12 cps, at a jetting temperature of from about 60° C. to about 100° C. such as about 80° C. to about 100° C., for example from about 90° C. to about 100° C. High energy inks are solid at a temperature below 40° C. and have a viscosity of from about 5 to about 15 cps at a jetting temperature of from about 100° C. to about 180° C., for example from 120° C. to about 160° C. or from about 125° C. to about 150° C.

Waxes can form a significant component of phase change inks. Many waxes exhibit undesirable characteristics such as low melting point and poor robustness. There is a need for modified waxes with increased melting point and improved properties, such as softening point. There is further a need for materials that are able to function as wax modifiers, gelating agents or gelators. There is further a need for materials that can function as gelators or modifying agents for waxes, hydrocarbons, organic liquids, creams, gels, cosmetics, or other materials.

The appropriate components and process aspects of the each of the foregoing U.S. Patents and Patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is a compound of the formula

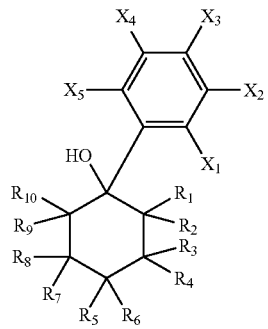

wherein $R_1, R_2, R_3, R_4, R_5, R_6, R_7, R_8, R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof; wherein $X_1, X_2, X_3, X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can optionally be a mixture of cis and trans isomers wherein only one of $R_1$ to $R_{10}$ is a non-hydrogen group.

Also described is a composition comprising a carrier; and a compound of the formula

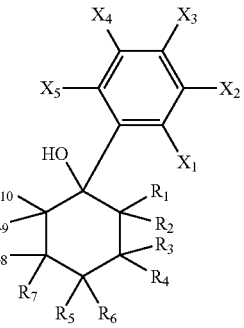

wherein $R_1, R_2, R_3, R_4, R_5, R_6, R_7, R_8, R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof; wherein $X_1, X_2, X_3, X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can optionally be a mixture of cis and trans isomers wherein only one of $R_1$ to $R_{10}$ is a non-hydrogen group.

Also described is a phase change ink comprising a carrier; an optional colorant; and a compound of the formula

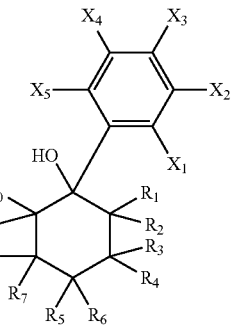

wherein $R_1, R_2, R_3, R_4, R_5, R_6, R_7, R_8, R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof; wherein $X_1, X_2, X_3, X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can optionally be a mixture of cis and trans isomers wherein only one of $R_1$ to $R_{10}$ is a non-hydrogen group.

Also described is an ink jet printer stick or pellet containing a phase change ink composition comprising a carrier; an optional colorant; and a compound of the formula

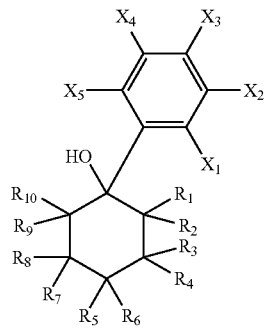

wherein $R_1$, $R_2$, $R_3$, $R_4$, $R_5$, $R_6$, $R_7$, $R_8$, $R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof; wherein $X_1$, $X_2$, $X_3$, $X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can optionally be a mixture of cis and trans isomers wherein only one of $R_1$ to $R_{10}$ is a non-hydrogen group.

DETAILED DESCRIPTION

The gelator compounds herein are suitable for numerous applications in industries ranging from oil and gas to inks to personal care products, such as makeup, creams, and lotions. The compounds are suitable for use in compositions including, but not limited to, hot-melt or phase change inks, creams, gels, cosmetics. The compounds can be used to modify or gelate materials including, but not limited to, hydrocarbons, waxes, oil, solvent, water, organic liquid, inorganic liquid, and other materials. The gelator compounds are low-cost and, in embodiments, can be bio-based materials. In specific embodiments, the gelator compounds herein are suitable for use in creams, makeup, and lotions.

The gelator compounds herein can be used for enhancing the properties of waxes to increase the melting point and softening temperature. Waxes are used in many applications including phase change solid inks. There exists a need to widen the scope of these materials for improved robustness and modify their properties. For example, most waxes have melting points ranging from 50 to 70° C., but many applications require waxes that melt at 120° C. or higher.

In embodiments, the gelator compounds provided herein are phenylcyclohexanol derivatives. The gelator molecules can be synthesized from the reaction of alkyl- or aryl-magnesium halide and ketone.

In embodiments, the gelator compound is a phenylcyclohexanol derivative comprising a compound of the formula

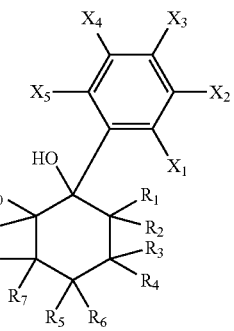

wherein $R_1$, $R_2$, $R_3$, $R_4$, $R_5$, $R_6$, $R_7$, $R_8$, $R_9$, and $R_{10}$ are each independently selected from a member of the group consisting of hydrogen, alkyl, aryl, arylalkyl, alkylaryl, straight-chain hydrocarbon, branched-chain hydrocarbon, halogen, and mixtures thereof;

wherein $X_1$, $X_2$, $X_3$, $X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein if one of the groups $R_1$ to $R_{10}$ are non-hydrogen, the compound can be a mixture of cis and trans isomers.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

In embodiments, the alkyl group may have 1 to 40 carbon atoms (whenever it appears herein, a numerical range such as "1 to 40" refers to each integer in the given range; e.g., "1 to 40 carbon atoms" means that the alkyl group may consist of 1 carbon atom, 2 carbon atoms, 3 carbon atoms, etc., up to and including 40 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 4 carbon atoms. The alkyl group of the compounds of the invention may be designated as "C 1-C 4 alkyl" or similar designations. By way of example only, "C 1-C 4 alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

In embodiments, the alkyl group may be substituted or unsubstituted. When substituted, any group(s) besides hydrogen can be the substituent group(s). When substituted, the substituent group(s) is(are) one or more group(s) individually and independently selected from the following non-limiting illustrative list: alkyl, cycloalkyl, hydroxy, alkoxy, cyano, halo, and amino, including mono- and di-substituted amino groups. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Each substituent group may be further substituted.

The term "aryl," as used herein, alone or in combination, means a carbocyclic aromatic system containing one, two or three rings wherein such rings may be attached together in a pendent manner or may be fused. The term "aryl," embraces aromatic radicals such as benzyl, phenyl, naphthyl, anthracenyl, and biphenyl.

The term "arylalkyl" as used herein, alone or in combination, refers to an aryl group attached to the parent molecular moiety through an alkyl group. The term "alkanediyl" refers to a divalent radical of an alkane group. Such alkanediyl has a general formula —Cn(RxRy)n-, where each Rx and Ry are independently a lower alkyl group or hydrogen.

The term "alkylaryl" as used herein, alone or in combination, refers to an alkyl group attached to the parent molecular moiety through an aryl group.

In embodiments, the gelator compound is a compound is of the formula

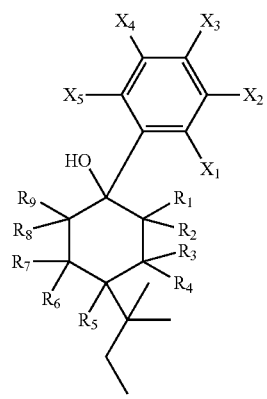

wherein $R_1$, $R_2$, $R_3$, $R_4$, $R_5$, $R_6$, $R_7$, $R_8$, and $R_9$ are each independently selected from a member of the group consisting of hydrogen, alkyl, aryl, arylalkyl, alkylaryl, straight-chain hydrocarbon, branched-chain hydrocarbon, halogen, and mixtures thereof;

wherein $X_1$, $X_2$, $X_3$, $X_4$, and $X_5$ are each independently selected from a member of the group consisting of hydrogen, alkyl, aryl, arylalkyl, alkylaryl, alkoxyl, aryloxy, straight-chain hydrocarbon, branched-chain hydrocarbon, halogen, and mixtures thereof; and wherein the compound can be a cis and trans mixture.

In embodiments, $R_1$, $R_2$, $R_3$, $R_4$, $R_5$, $R_6$, $R_7$, $R_8$, and $R_9$ are each hydrogen and $X_1$, $X_2$, $X_3$, $X_4$, and $X_5$ are each hydrogen.

In embodiments, at least one of $R_1$, $R_2$, $R_3$, $R_4$, $R_5$, $R_6$, $R_7$, $R_8$, and $R_9$ is alkyl.

In other embodiments, at least one of $R_1$, $R_2$, $R_3$, $R_4$, $R_5$, $R_6$, $R_7$, $R_8$, and $R_9$ is alkyl, and $X_1$, $X_2$, $X_3$, $X_4$, and $X_5$ are each hydrogen.

In specific embodiments, the gelator is a compound comprising a cis and trans mixture of the formula

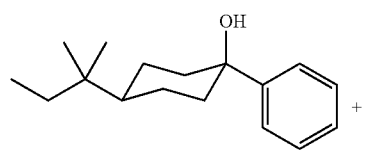

+

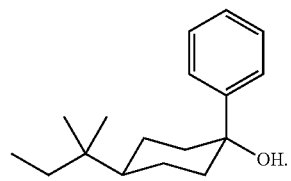

In other specific embodiments, the gelator is a compound comprising a cis and trans mixture of the formula

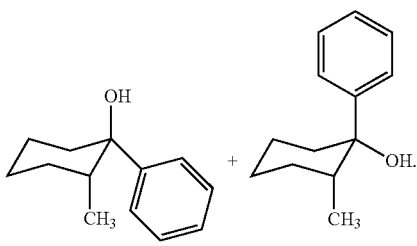

In other specific embodiments, the gelator is a compound comprising a cis and trans mixture of the formula

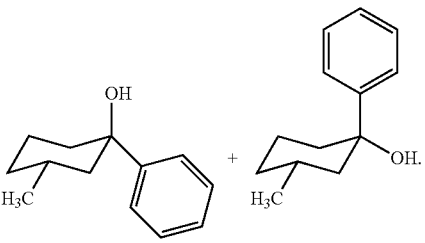

In other specific embodiments, the gelator is a compound comprising a cis and trans mixture of the formula

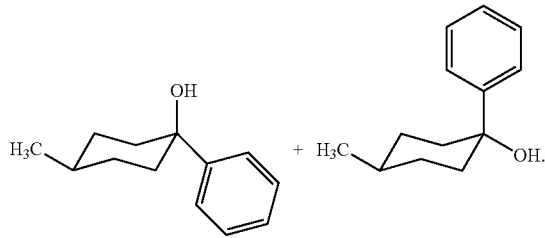

The gelator compounds herein can be prepared by any suitable or desired method. In embodiments, the gelator compounds can be prepared by the reaction between an alkyl- or aryl-magnesium halide (Grignard reagent) with a ketone.

In a specific embodiment, the gelator compounds contain a 4-tert-pentyl group on the ketone moiety.

In embodiments, the gelator compound herein comprises a cis/trans (4-tert-pentyl)-1-phenyl cyclohexanol prepared by the following reaction scheme.

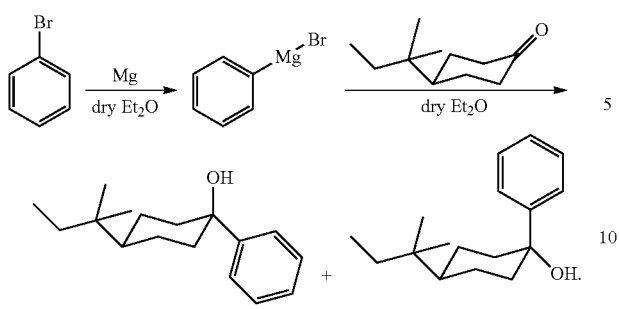

In embodiments, the gelator compound herein comprises a cis/trans 2-methyl-1-phenyl cyclohexanol prepared by the following reaction scheme.

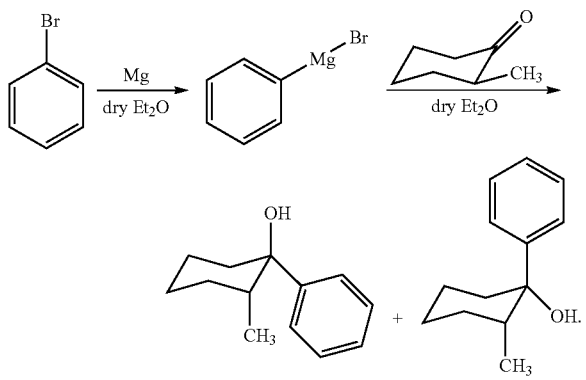

In embodiments, the gelator compound herein comprises a cis/trans 3-methyl-1-phenyl cyclohexanol prepared by the following reaction scheme.

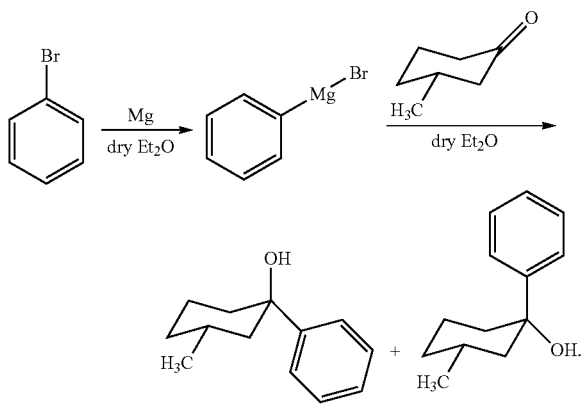

In embodiments, the gelator compound herein comprises a cis/trans 4-methyl-1-phenyl cyclohexanol prepared by the following reaction scheme.

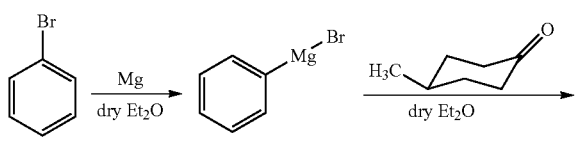

-continued

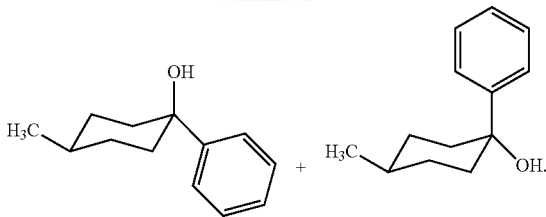

The present disclosure further provides a composition comprising a carrier; and a gelator compound of the formula as described herein. The carrier can be any suitable or desired carrier for the intended composition. In embodiments, the carrier comprises a member of the group consisting of wax, oil, solvent, water, organic liquid, hydrocarbon liquid, inorganic liquid, and combinations thereof. In certain embodiments, the carrier comprises at least one wax having a melting point of 120° C. or higher.

In certain embodiments, a phase change ink is provided comprising a carrier; an optional colorant; and a gelator compound of the formula as described herein.

In embodiments, the phase change ink carrier comprises at least one wax. In specific embodiments, the phase change ink carrier comprises at least one wax having a melting point of 120° C. or higher.

The phase change ink compositions herein can include any suitable ink carrier or vehicle, such as paraffins, microcrystalline waxes, polyethylene waxes, ester waxes, amides, fatty acids and other waxy materials, fatty amide containing materials, sulfonamide materials, resinous materials made from different natural sources (tall oil rosins and rosin esters, for example), and many synthetic resins, oligomers, polymers, and copolymers such as further discussed below.

In embodiments, the phase change ink compositions herein include a polyalkylene wax carrier, in embodiments, a polymethylene wax, a polyethylene wax, or a mixture of combination thereof.

In certain embodiments, the phase change ink compositions herein include a biodegradable wax carrier. In embodiments, the biodegradable wax is a biodegradable polyethylene wax. For example, the wax can be a compostable/biodegradable polyethylene wax such as are available from companies such as The International Group, Inc. and Sasol Wax.

In embodiments, the phase change ink compositions herein further comprises a low melting wax carrier. In embodiments, the low melting wax is a polyalkylene wax, a functional wax, or a combination thereof. The term "functional wax" is known to one of skill in the art and can mean herein any suitable functional wax, in embodiments, including, but not limited to, a wax with polar groups, for example, alcohols, amides, esters, urethanes, etc. As used herein, the term "low melting wax" includes any suitable low melting wax, including, in embodiments, a wax having a melting point of less than about 120° C.

The phase change ink carrier can comprise suitable amides, for example, diamides, triamides, tetra-amides, cyclic amides and the like.

The ink jet vehicle or carrier can be present in the phase change ink composition in any suitable or desired amount. In embodiments, the carrier is present in the phase change ink composition in an amount of from about 25 percent to about 65 percent by weight based on the total weight of the phase change ink composition. In embodiments, the carrier is a low melting wax present in the phase change ink composition in an amount of from about 25% to less than about 65% by weight based on the total weight of the ink carrier.

Other suitable carrier materials that can be used in the phase change ink composition include isocyanate-derived resins and waxes, such as urethane isocyanate-derived materials, urea isocyanate-derived materials, urethane/urea isocyanate-derived materials, mixtures thereof, and the like. Further information on isocyanate-derived carrier materials is disclosed in, for example, U.S. Pat. Nos. 5,750,604, 5,780, 528, 5,782,966, 5,783,658, 5,827,918, 5,830,942, 5,919,839, 6,255,432, and 6,309,453, British Patents Nos. GB 2 294 939, GB 2 305 928, GB 2 305 670, and GB 2 290 793, and PCT Publications WO 94/14902, WO 97/12003, WO 97/13816, WO 96/14364, WO 97/33943, and WO 95/04760, the entire disclosures of each of which are incorporated herein by reference. In embodiments, the phase change ink composition can contain a mixture of one or more amides and one or more isocyanate-derived materials.

Further examples of suitable ink vehicles include ethylene/propylene copolymers, such as those available from Baker Petrolite. Commercial examples of such copolymers include, for example, Petrolite CP-7 (Mn=650), Petrolite CP-11 (Mn=1,100, Petrolite CP-12 (Mn=1,200) and the like. The copolymers may have, for example, a melting point of from about 70° C. to about 150° C., such as from about 80° C. to about 130° C. or from about 90° C. to about 120° C. and a molecular weight range (Mn) of from about 500 to about 4,000.

Another type of ink vehicle may be n-paraffinic, branched paraffinic, and/or naphthenic hydrocarbons, typically with from about 5 to about 100, such as from about 20 to about 80 or from about 30 to about 60 carbon atoms, generally prepared by the refinement of naturally occurring hydrocarbons, such as BE SQUARE 185 and BE SQUARE 195, with molecular weights (Mn) of from about 100 to about 5,000, such as from about 250 to about 1,000 or from about 500 to about 800, for example such as available from Baker Petrolite.

Highly branched hydrocarbons, typically prepared by olefin polymerization, such as the VYBAR materials available from Baker Petrolite, including VYBAR 253 (Mn=520), VYBAR 5013 (Mn=420), and the like, may also be used. In addition, the ink vehicle may be an ethoxylated alcohol, such as available from Baker Petrolite and of the general formula

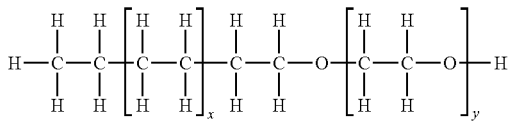

wherein x is an integer of from about 1 to about 50, such as from about 5 to about 40 or from about 11 to about 24 and y is an integer of from about 1 to about 70, such as from about 1 to about 50 or from about 1 to about 40. The materials may have a melting point of from about 60° C. to about 150° C., such as from about 70° C. to about 120° C. or from about 80° C. to about 110° C. and a molecular weight (Mn) range of from about 100 to about 5,000, such as from about 500 to about 3,000 or from about 500 to about 2,500. Commercial examples include UNITHOX 420 (Mn=560), UNITHOX 450 (Mn=900), UNITHOX 480 (Mn=2,250), UNITHOX 520 (Mn=700), UNITHOX 550 (Mn=1,100), UNITHOX 720 (Mn=875), UNITHOX 750 (Mn=1,400), and the like.

As an additional example, the ink vehicle may be made of fatty amides, such as monoamides, tetra-amides, mixtures thereof, and the like, for example such as described in U.S. Pat. No. 6,858,070, which is hereby incorporated herein by reference. Suitable monoamides may have a melting point of at least about 50° C., for example from about 50° C. to about 150° C., although the melting point can be outside these ranges. Specific examples of suitable monoamides include, for example, primary monoamides and secondary monoamides. Stearamide, such as KEMAMIDE S available from Witco Chemical Company and CRODAMIDE S available from Croda, behenamide/arachidamide, such as KEMAMIDE B available from Witco and CRODAMIDE BR available from Croda, oleamide, such as KEMAMIDE U available from Witco and CRODAMIDE OR available from Croda, technical grade oleamide, such as KEMAMIDE O available from Witco, CRODAMIDE O available from Croda, and UNISLIP 1753 available from Uniqema, and erucamide such as KEMAMIDE E available from Witco and CRODAMIDE ER available from Croda, are some examples of suitable primary amides. Behenyl behenamide, such as KEMAMIDE EX666 available from Witco, stearyl stearamide, such as KEMAMIDE S-180 and KEMAMIDE EX-672 available from Witco, stearyl erucamide, such as KEMAMIDE E-180 available from Witco and CRODAMIDE 212 available from Croda, erucyl erucamide, such as KEMAMIDE E-221 available from Witco, oleyl palmitamide, such as KEMAMIDE P-181 available from Witco and CRODAMIDE 203 available from Croda, and erucyl stearamide, such as KEMAMIDE S-221 available from Witco, are some examples of suitable secondary amides. Additional suitable amide materials include KEMAMIDE W40 (N,N'-ethylenebisstearamide), KEMAMIDE P181 (oleyl palmitamide), KEMAMIDE W45 (N,N'-ethylenebisstearamide), and KEMAMIDE W20 (N,N'-ethylenebisoleamide). In embodiments, the phase change ink composition can comprise stearyl stearamide, triamide, or mixtures thereof.

High molecular weight linear alcohols, such as those available from Baker Petrolite and of the general formula

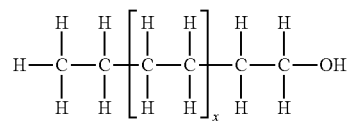

wherein x is an integer of from about 1 to about 50, such as from about 5 to about 35 or from about 11 to about 23, may also be used as the ink vehicle. These materials may have a melting point of from about 50° C. to about 150° C., such as from about 70° C. to about 120° C. or from about 75° C. to about 110° C., and a molecular weight (Mn) range of from about 100 to about 5,000, such as from about 200 to about 2,500 or from about 300 to about 1,500. Commercial examples include the UNILIN materials such as UNILIN 425 (Mn=460), UNILIN 550 (Mn=550), UNILIN 700 (Mn=700), and distilled alcohols, the viscosity of which at the jetting temperature in one embodiment can be from about 5 to about 50% higher than the non-distilled alcohol.

A still further example includes hydrocarbon-based waxes, such as the homopolymers of polyethylene available from Baker Petrolite and of the general formula

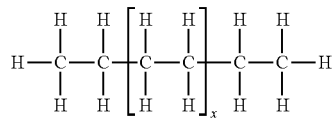

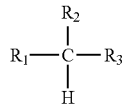

wherein $R_1$ and $R_3$ are hydrocarbon groups and $R_2$ is either of one of the general formulas

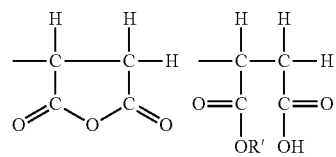

or a mixture thereof, wherein R' is an isopropyl group, which materials may have melting points of from about 70° C. to about 150° C., such as from about 80° C. to about 130° C. or from about 90° C. to about 125° C., with examples of modified maleic anhydride copolymers including CERAMER 67 (Mn=655, Mw/Mn=1.1), CERAMER 1608 (Mn=700, Mw/Mn=1.7), and the like.

wherein x is an integer of from about 1 to about 200, such as from about 5 to about 150 or from about 12 to about 105. These materials may have a melting point of from about 60° C. to about 150° C., such as from about 70° C. to about 140° C. or from about 80° C. to about 130° C. and a molecular weight (Mn) of from about 100 to about 5,000, such as from about 200 to about 4,000 or from about 400 to about 3,000. Example waxes include PW400 (Mn about 400), distilled PW400, in one embodiment having a viscosity of about 10% to about 100% higher than the viscosity of the undistilled POLYWAX® 400 at about 110° C., POLYWAX 500 (Mn about 500), distilled POLYWAX® 500, in one embodiment having a viscosity of about 10% to about 100% higher than the viscosity of the undistilled POLYWAX® 500 at about 110° C., POLYWAX 655 (Mn about 655), distilled POLYWAX® 655, in one embodiment having a viscosity of about 10% to about 50% lower than the viscosity of the undistilled POLYWAX® 655 at about 110° C., and in yet another embodiment having a viscosity of about 10% to about 50% higher than the viscosity of the undistilled POLYWAX® 655 at about 110° C. POLYWAX 850 (Mn about 850), POLYWAX 1000 (Mn about 1,000), and the like.

Another example includes modified maleic anhydride hydrocarbon adducts of polyolefins prepared by graft copolymerization, such as those available from Baker Petrolite and of the general formulas

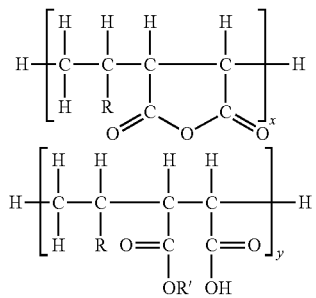

wherein R is an alkyl group with from about 1 to about 50, such as from about 5 to about 35 or from about 6 to about 28 carbon atoms, R' is an ethyl group, a propyl group, an isopropyl group, a butyl group, an isobutyl group, or an alkyl group with from about 5 to about 500, such as from about 10 to about 300 or from about 20 to about 200 carbon atoms, x is an integer of from about 9 to about 13, and y is an integer of from about 1 to about 50, such as from about 5 to about 25 or from about 9 to about 13, and having melting points of from about 50° C. to about 150° C., such as from about 60° C. to about 120° C. or from about 70° C. to about 100° C.; and those available from Baker Petrolite and of the general formula Additional examples of suitable ink vehicles for the phase change inks include rosin esters; polyamides; dimer acid amides; fatty acid amides, including ARAMID C; epoxy resins, such as EPOTUF 37001, available from Riechold Chemical Company; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides, including KETJENFLEX MH and KETJENFLEX MS80; benzoate esters, such as BENZOFLEX 5552, available from Velsicol Chemical Company; phthalate plasticizers; citrate plasticizers; maleate plasticizers; sulfones, such as diphenyl sulfone, n-decyl sulfone, n-amyl sulfone, chlorophenyl methyl sulfone; polyvinyl pyrrolidinone copolymers; polyvinyl pyrrolidone/polyvinyl acetate copolymers; novolac resins, such as DUREZ 12 686, available from Occidental Chemical Company; and natural product waxes, such as beeswax, monton wax, candelilla wax, GILSONITE (American Gilsonite Company), and the like; mixtures of linear primary alcohols with linear long chain amides or fatty acid amides, such as those with from about 6 to about 24 carbon atoms, including PARICIN 9 (propylene glycol monohydroxystearate), PARICIN 13 (glycerol monohydroxystearate), PARICIN 15 (ethylene glycol monohydroxystearate), PARICIN 220 (N(2-hydroxyethyl)-12-hydroxystearamide), PARICIN 285 (N,N'-ethylene-bis-12-hydroxystearamide), FLEXRICIN 185 (N,N'-ethylene-bis-ricinoleamide), and the like. Further, linear long chain sulfones with from about 4 to about 16 carbon atoms, such as n-propyl sulfone, n-pentyl sulfone, n-hexyl sulfone, n-heptyl sulfone, n-octyl sulfone, n-nonyl sulfone, n-decyl sulfone, n-undecyl sulfone, n-dodecyl sulfone, n-tridecyl sulfone, n-tetradecyl sulfone, n-pentadecyl sulfone, n-hexadecyl sulfone, and the like, are suitable ink vehicle materials.

In addition, the ink vehicles described in U.S. Pat. No. 6,906,118, which is incorporated herein by reference, may also be used. The ink vehicle may contain a branched triamide such as those described in U.S. Pat. No. 6,860,930, the disclosure of which is also incorporated by reference herein,

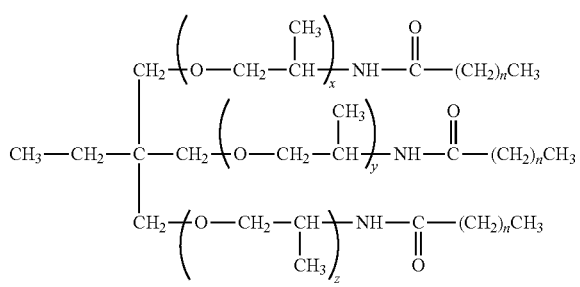

wherein n has an average value of from about 34 equal to or less than 40, where x, y and z can each be zero or an integer, and wherein the sum of x, y, and z is from about 5 and equal to or less than 6.

Optionally, a plasticizer, which can be either a solid or liquid plasticizer, such as benzyl phthalates, triaryl phosphate esters, pentaerythritol tetrabenzoate, dialkyl adipate, dialkyl phthalates, dialkyl sebacate, alkyl benzyl phthalates, ethylene glycol monostearate, glycerol monostearate, propylene glycol monostearate, dicyclohexyl phthalate, diphenyl isophthalate, triphenyl phosphate, dimethyl isophthalate, and mixtures thereof, or the like can also be included in the ink carrier. The plasticizer is present in the ink carrier in any desired or effective amount, such as from about 0.05% by weight of the ink carrier. Examples of suitable plasticizers include SANTICIZER® 278, SANTICIZER® 154, SANTICIZER®160, SANTICIZER® 261 (commercially available from Monsanto), and the like or mixtures thereof.

A hindered amine antioxidant can optionally be present in the ink in any desired or effective amount, such as from about 0.001 percent to about 0.50 percent by weight of the total ink composition.

Examples of suitable hindered amine antioxidants include those of general formula

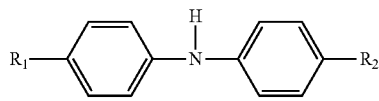

wherein $R_1$ and $R_2$ each, independently of the other, can be a hydrogen atom or an alkyl group, including linear, branched, saturated, unsaturated, cyclic, substituted, and unsubstituted alkyl groups, and wherein hetero atoms, such as oxygen, nitrogen, sulfur, silicon, phosphorus, boron, either may or may not be present in the alkyl group, in one embodiment with at least 1 carbon atom, if substituted, substitutions can be alkyl or phenyl.

Specific examples of suitable hindered amine antioxidants include the following antioxidants commercially available from Crompton; NAUGUARD® 445 where $R_1=R_2=C(CH_3)_2Ph$, NAUGUARD® 635 where $R_1=R_2=\!\!-\!\!CH(CH_3)Ph$, NAUGUARD® PS-30 where $R_1=C_4$ or $C_8$, $R_2=C_4$ or $C_8$ and the like.

A hindered phenol antioxidant can also be provided. In one embodiment the hindered phenol is present in a relatively high concentration. A high concentration of hindered phenol antioxidant maximizes long term thermal stability by delaying the onset of the oxidation itself. The hindered phenol antioxidant is present in the ink in any desired or effective amount, in embodiments from about 0.01% to about 4.0% by weight of the total ink composition. Specific examples of suitable hindered phenol antioxidants include ETHANOX® 330, ETHANOX® 310, ETHANOX® 314, ETHANOX® 376 (commercially available from Albemarle) and the like. Also commercially available from BASF SE are IRGANOX® 1010, IRGANOX® 1035, IRGANOX®1076, IRGANOX® 1330 and the like. Mixtures of two or more of these hindered phenol antioxidants can also be employed.

A rosin ester resin, mixtures thereof, or the like can also be included in the phase change ink composition. The rosin ester resin is present in any desired or effective amount, in embodiments from 0.5% to about 20% by weight of the total ink composition. Examples of suitable rosin ester resins include Pinecrystal KE-100 (commercially available from Arakawa), and the like.

The phase change ink composition can include ink carrier, in embodiments comprising wax and other optional carrier components, in any desired or effective amount, in embodiments in an amount of at least about 50% by weight of the ink to equal to or less than about 99% by weight of the ink. In certain embodiments, in an amount of from about 25% to about 65% by total weight of the phase change ink composition.

In one specific embodiment, the ink carrier has a melting point of less than about 110° C., and in another embodiment of less than about 100° C., although the melting point of the ink carrier can be outside of these ranges.

Colorant.

The phase change ink compositions can include any suitable or desired colorant such as colorants selected from the group consisting of traditional dyes, pigments, and mixtures and combinations thereof present in any suitable or desired amount. If more than one colorant is included, the total amount of colorant present in the phase change ink composition can be any desired or effective amount to obtain the desired color or hue, in embodiments from about 0.1 to about 50 percent, or from about 0.1 percent to about 20 percent total colorant by weight based on the total weight of the phase change ink composition.

Any desired or effective colorant can be employed in the inks, including dyes, pigments, mixtures thereof, and the like, provided that the colorant can be dissolved or dispersed in the ink vehicle. The compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like.

Examples of suitable dyes include Neozapon® Red 492 (BASF); Orasol® Red G (Pylam Products); Direct Brilliant Pink B (Oriental Giant Dyes); Direct Red 3BL (Classic Dyestuffs); Supranol® Brilliant Red 3BW (Bayer AG); Lemon Yellow 6G (United Chemie); Light Fast Yellow 3G (Shaanxi); Aizen Spilon Yellow C-GNH (Hodogaya Chemical); Bemachrome Yellow GD Sub (Classic Dyestuffs); Cartasol® Brilliant Yellow 4GF (Clariant); Cibanone Yellow 2G (Classic Dyestuffs); Orasol® Black RLI (BASF); Orasol® Black CN (Pylam Products); Savinyl Black RLSN(Clariant); Pyrazol Black BG (Clariant); Morfast® Black 101 (Rohm & Haas); Diaazol Black RN (ICI); Thermoplast® Blue 670 (BASF); Orasol® Blue GN (Pylam Products); Savinyl Blue GLS (Clariant); Luxol Fast Blue MBSN (Pylam Products); Sevron Blue 5GMF (Classic Dyestuffs); Basacid® Blue 750 (BASF); Keyplast Blue (Keystone Aniline Corporation); Neozapon® Black X51 (BASF); Classic Solvent Black 7 (Classic Dyestuffs); Sudan Blue 670 (C.I. 61554) (BASF); Sudan Yellow 146 (C.I. 12700) (BASF); Sudan Red 462 (C.I. 26050) (BASF); C.I. Disperse Yellow 238; Neptune Red Base NB543 (BASF, C.I. Solvent Red 49); Neopen® Blue FF-4012 (BASF); Fastol® Black BR(C.I. Solvent Black 35) (Chemische Fabriek Triade BV); Morton Morplas Magenta 36 (C.I. Solvent Red 172); metal phthalocyanine colorants, such as those disclosed in U.S. Pat. No. 6,221,137, the disclosure of which is totally incorporated herein by reference, and the like. Polymeric dyes can also be used, such as those disclosed in, for example, U.S. Pat. Nos. 5,621,022 and 5,231,135, the disclosures of each of which are hereby incorporated by reference herein in their entireties, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactint® Orange X-38, uncut Reactint® Blue X-17, Solvent Yellow 162, Acid Red 52, Solvent Blue 44, and uncut Reactint® Violet X-80.

In specific embodiments, the phase change ink compositions herein are pigmented phase change ink compositions. In embodiments, the pigment is selected from the group consisting of metal phthalocyanine, metal-free phthalocyanine, and mixtures and combinations thereof. In certain embodiments, the phase change ink composition includes a pigment selected from the group consisting of cyan, green, blue, black, carbon black, Pigment Blue, copper phthalocyanine, and mixtures and combinations thereof. In a specific embodiment, the pigment is a cyan pigment.

Suitable pigments that can be used in embodiments herein include, for example, PALIOGEN® Violet 5100 (commercially available from BASF); PALIOGEN® Violet 5890 (commercially available from BASF); HELIOGEN® Green L8730 (commercially available from BASF); LITHOL® Scarlet D3700 (commercially available from BASF); SUNFAST® Blue 15:4 (commercially available from Sun Chemical); HOSTAPERM® Blue B2G-D (commercially available from Clariant); HOSTAPERM® Blue B4G (commercially available from Clariant); Permanent Red P—F7RK; HOSTAPERM® Violet BL (commercially available from Clariant); LITHOL® Scarlet 4440 (commercially available from BASF); Bon Red® C (commercially available from Dominion Color Company); ORACET® Pink RF (commercially available from Ciba); PALIOGEN® Red 3871 K (commercially available from BASF); SUNFAST® Blue 15:3 (commercially available from Sun Chemical); PALIOGEN® Red 3340 (commercially available from BASF); SUNFAST® Carbazole Violet 23 (commercially available from Sun Chemical); LITHOL® Fast Scarlet L4300 (commercially available from BASF); SUNBRITE® Yellow 17 (commercially available from Sun Chemical); HELIOGEN® Blue L6900, L7020 (commercially available from BASF); SUNBRITE® Yellow 74 (commercially available from Sun Chemical); SPECTRA® PAC C Orange 16 (commercially available from Sun Chemical); HELIOGEN® Blue K6902, K6910 (commercially available from BASF); SUNFAST® Magenta 122 (commercially available from Sun Chemical); HELIOGEN® Blue D6840, D7080 (commercially available from BASF); Sudan Blue OS (commercially available from BASF); NEOPEN® Blue FF4012 (commercially available from BASF); PV Fast Blue B2GO1 (commercially available from Clariant); IRGALITE® Blue BCA (commercially available from Ciba); PALIOGEN® Blue 6470 (commercially available from BASF); Sudan Orange G (commercially available from Aldrich), Sudan Orange 220 (commercially available from BASF); PALIOGEN® Orange 3040 (BASF); PALIOGEN® Yellow 152, 1560 (commercially available from BASF); LITHOL® Fast Yellow 0991 K (commercially available from BASF); PALIOTOL® Yellow 1840 (commercially available from BASF); NOVOPERM® Yellow FGL (commercially available from Clariant); Ink Jet Yellow 4G VP2532 (commercially available from Clariant); Toner Yellow HG (commercially available from Clariant); Lumogen® Yellow D0790 (commercially available from BASF); Suco-Yellow L1250 (commercially available from BASF); Suco-Yellow D1355 (commercially available from BASF); Suco Fast Yellow D1 355, D1 351 (commercially available from BASF); HOSTAPERM® Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL® Pink D4830 (commercially available from BASF); CINQUASIA® Magenta (commercially available from DU PONT); PALIOGEN® Black L0084 (commercially available from BASF); Pigment Black K801 (commercially available from BASF); and carbon blacks such as REGAL® 330 (commercially available from Cabot), Nipex® 150 (commercially available from Degussa) Carbon Black 5250 and Carbon Black 5750 (commercially available from Columbia Chemical), and the like, as well as mixtures thereof.

The pigment can be provided in the phase change ink composition in any suitable or desired amount. In embodiments, the pigment can be present in an amount of from about 0.1 to about 20 percent, or from about 0.5 percent to about 5 percent, or about 0.75 to about 3 percent total pigment, based on the total weight of the phase change ink composition.

The phase change ink compositions disclosed herein in one embodiment have melting points in one embodiment equal to or less than about 130° C., in another embodiment equal to or less than about 120° C., in a further embodiment equal to or less than about 110° C., and in still another embodiment equal to or less than about 100° C., although the melting point can be outside of these ranges.

The phase change ink compositions prepared by the process disclosed herein generally have melt viscosities, at the jetting temperature which can be equal to or less than about 145° C., in one embodiment equal to or less than about 130° C., and in another embodiment equal to or less than about 120° C., in a further embodiment equal to or less than about 110° C., and in yet another embodiment equal to or less than about 80° C., although the jetting temperature can be outside of these ranges, which are in one embodiment equal to or less than about 30 centipoise (cps), in another embodiment equal to or less than about 25 cps, and in yet a further embodiment equal to or less than about 20 cps, and in another embodiment no less than about 2 cps, in a further embodiment no less than about 3 cps, and in yet a further embodiment no less than about 4 cps, although the melt viscosity can be outside of these ranges.

In certain embodiments, the phase change ink composition herein has a jetting temperature of from about 100° C. to about 130° C.

In embodiments, the phase change ink composition herein has a viscosity of about 9 to about 12 centipoise at 110° C. In certain embodiments, the phase change ink composition herein has a viscosity of about 10 centipoise at 110° C.

The phase ink compositions of the present disclosure can be prepared by any desired or suitable method. In embodiments, a method for preparing a phase change ink composition comprises combining a carrier; a gelator compound, and an optional colorant, to produce a phase change ink composition. For example, the ink ingredients can be mixed together, followed by heating, to a temperature of at least about 100° C. to no more than about 140° C., although the temperature can be outside of this range, and stiffing until a homogeneous ink composition is obtained, followed by cooling the ink to ambient temperature (typically from about 20 to about 25° C.). The inks of the present disclosure are solid at ambient temperature. In a specific embodiment, during the formation process, the inks in their molten state are poured into molds and then allowed to cool and solidify to form ink sticks. In embodiments, an ink jet printer stick or pellet herein contains a phase change ink composition comprising a carrier; a gelator compound, and an optional colorant.

The inks disclosed herein can be employed in apparatus for direct printing ink jet processes and in indirect (offset) printing ink jet applications. Another embodiment is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195, 430, the disclosure of which is totally incorporated herein by reference. The inks prepared as disclosed herein can be employed in apparatus for indirect (offset) printing ink jet applications. Another embodiment is directed to a process which comprises incorporating an ink prepared as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements.

Any suitable substrate or recording sheet can be employed, including plain papers such as XEROX® 4024 papers, XEROX® Image Series papers, Courtland 4024 DP paper, ruled notebook paper, bond paper, silica coated papers such as Sharp Company silica coated paper, JuJo paper, Hammermill Laserprint Paper, and the like, transparency materials, fabrics, textile products, plastics, polymeric films, inorganic substrates such as metals and wood, and the like.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Example 1

Preparation of cis/trans 4-tert-pentyl-1-phenyl cyclohexanol

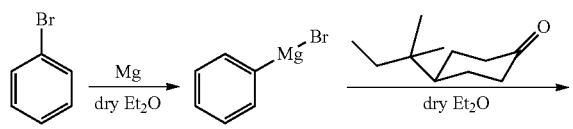

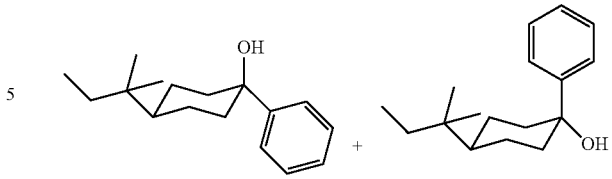

To an oven-dried 1 liter 3-necked round-bottomed flask with a stir-bar and fitted with a dropping funnel and reflux condenser was added acid-washed, ethanol rinsed, dried magnesium (13.5 grams, 555 mmol), followed by diethyl ether (Volume: 250 milliliters) transferred via cannula. The dropping funnel was charged with bromobenzene (57.0 milliliters, 541 mmol), an $I_2$ crystal was added to the reaction flask to initiate the reaction, and the bromide was added dropwise to maintain a steady reflux of ether. The addition was completed over 30 minutes' time. Next, the dropping funnel was charged with 4-(tert-pentyl)cyclohexanone (Orivone™) (76 grams, 0.45 mol), and the ketone was slowly added dropwise into the Grignard solution with stiffing over an hour, and the reaction was allowed to proceed overnight at room temperature. The reaction contents were carefully poured into a beaker of ice and 300 milliliters 10% $NH_4Cl$ mixture to hydrolyze the Mg salts. The ethanol was removed from the suspension via rotovap, and 750 milliliters of dichloromethane was added. The mixture was transferred to a 1 liter separation funnel, and the dichloromethane layer was successively extracted with saturated bicarbonate solution brine solutions. Finally, the dichloromethane layer was dried with $MgSO_4$, filtered and the solvent was evaporated by rotovap to furnish 91 grams (369 mmol, 68.2% yield) of cis/trans 4-tertpentyl-1-phenyl cyclohexanol as a beige fragrant powder.

The structure of the cis/trans product mixture was confirmed by $^1$H NMR spectroscopy (400 MHz, $CDCl_3$): δ 7.58-7.28 (m, 5H, $C_6H_5$), 2.58 (d, 2H, cyclohexyl C-2 $H_{eq}$), 1.79-1.69 (m, 6H, cyclohexyl C-2 $H_{ax}$, C-3 $H_{ax}$ and $H_{eq}$), 1.34 (m, 1H, cyclohexyl C-4 $H_{ax}$ (trans isomer)), 1.21 (m, 1H, cyclohexyl C-4 $H_{ax}$ (cis isomer)), 1.06 (q, 2H, $CH_3CH_2C(CH_3)_2$), 0.80 (t, 3H, $CH_3CH_2$), 0.72 (s, 6H, $CH_3CH_2C(CH_3)_2$)

Example 2

Preparation of cis/trans 2-methyl-1-phenyl cyclohexanol (Prophetic)

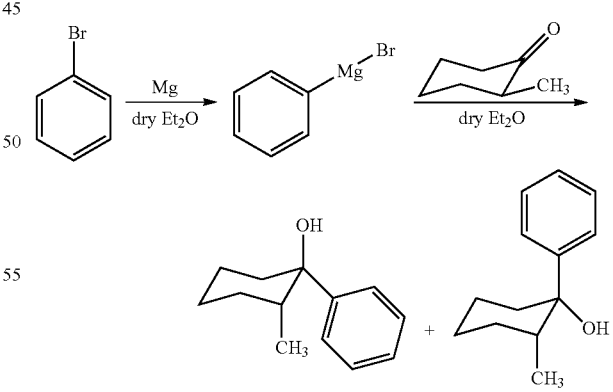

To an oven-dried 1 liter, 3-necked round-bottomed flask with a stir-bar and fitted with a dropping funnel and reflux condenser is added acid-washed, ethanol rinsed, dried magnesium (13.5 grams, 555 mmol), followed by diethyl ether (Volume: 250 milliliters) transferred via cannula. The dropping funnel is charged with bromobenzene (57.0 milliliters, 541 mmol), an $I_2$ crystal is added to the reaction flask to initiate the reaction, and the bromide is added dropwise to maintain a steady reflux of ether. The addition is completed over 30 minutes' time. Next, the dropping funnel is charged with 2-methylcyclohexanone (50.5 grams, 0.45 mol), and the ketone is slowly added dropwise into the Grignard solution with stirring over an hour, and the reaction is allowed to proceed overnight at room temperature. The reaction contents are carefully poured into an beaker of ice and 300 milliliters 10% NH$_4$Cl mixture to hydrolyze the Mg salts. The ethanol is removed from the suspension via rotovap, and 750 milliliters of dichloromethane is added. The mixture is then transferred to a 1 liter separation funnel, and the dichloromethane layer is successively extracted with saturated bicarbonate and brine solutions. Finally, the dichloromethane layer is dried with MgSO$_4$, filtered and the solvent is evaporated by rotovap to furnish cis/trans 2-methyl-1-phenyl cyclohexanol product.

Example 3

Preparation of cis/trans 3-methyl-1-phenyl cyclohexanol (Prophetic)

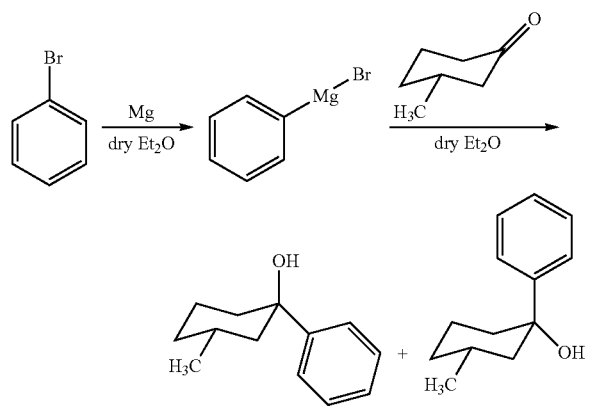

To an oven-dried 1 liter, 3-necked round-bottomed flask with a stir-bar and fitted with a dropping funnel and reflux condenser is added acid-washed, ethanol rinsed, dried magnesium (13.5 grams, 555 mmol), followed by diethyl ether (Volume: 250 milliliters) transferred via cannula. The dropping funnel is charged with bromobenzene (57.0 milliliters, 541 mmol), an I$_2$ crystal is added to the reaction flask to initiate the reaction, and the bromide is added dropwise to maintain a steady reflux of ether. The addition is completed over 30 minutes' time. Next, the dropping funnel is charged with 3-methylcyclohexanone (50.5 grams, 0.45 mol), and the ketone is slowly added dropwise into the Grignard solution with stirring over an hour, and the reaction is allowed to proceed overnight at room temperature. The reaction contents are carefully poured into a beaker of ice and 300 milliliters 10% NH$_4$Cl mixture to hydrolyze the Mg salts. The ethanol is removed from the suspension via rotovap, and 750 milliliters of dichloromethane is added. The mixture is then transferred to a 1 liter separation funnel, and the dichloromethane layer is successively extracted with saturated bicarbonate and brine solutions. Finally, the dichloromethane layer is dried with MgSO$_4$, filtered and the solvent is evaporated by rotovap to furnish cis/trans 3-methyl-1-phenyl cyclohexanol product.

Example 4

Preparation of cis/trans 4-methyl-1-phenyl cyclohexanol (Prophetic)

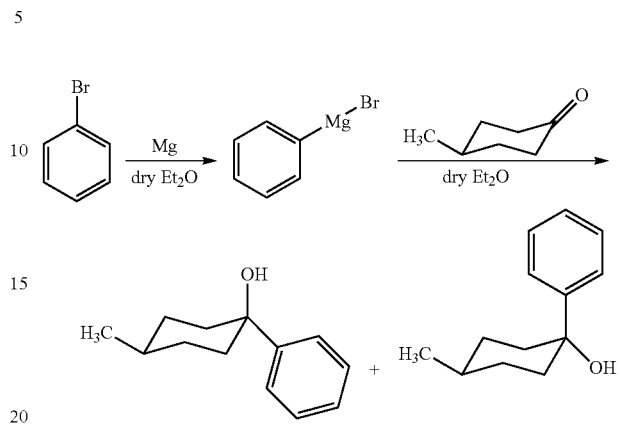

To an oven-dried 1 liter, 3-necked round-bottomed flask with a stir-bar and fitted with a dropping funnel and reflux condenser is added acid-washed, ethanol rinsed, dried magnesium (13.5 grams, 555 mmol), followed by diethyl ether (Volume: 250 milliliters) transferred via cannula. The dropping funnel is charged with bromobenzene (57.0 milliliters, 541 mmol), an I$_2$ crystal is added to the reaction flask to initiate the reaction, and the bromide is added dropwise to maintain a steady reflux of ether. The addition is completed over 30 minutes' time. Next, the dropping funnel is charged with 4-methylcyclohexanone (50.5 grams, 0.45 mol), and the ketone is slowly added dropwise into the Grignard solution with stirring over an hour, and the reaction is allowed to proceed overnight at room temperature. The reaction contents are carefully poured into a beaker of ice and 300 milliliters 10% NH$_4$Cl mixture to hydrolyze the Mg salts. The ethanol is removed from the suspension via rotovap, and 750 milliliters of dichloromethane is added. The mixture is then transferred to a 1 liter separation funnel, and the dichloromethane layer is successively extracted with saturated bicarbonate and brine solutions. Finally, the dichloromethane layer is dried with MgSO$_4$, filtered and the solvent is evaporated by rotovap to furnish cis/trans 4-methyl-1-phenyl cyclohexanol product.

Gel Properties.

200 milligrams of gelator prepared in Example 1 was dissolved in 10 milliliters of dodecane solvent at 100° C. The clear solution was allowed to cool to room temperature, forming a soft, free-standing opaque gel.

Gelation Tests Through Drop Point Measurements.

The measurement of gel strength was determined by measurement of dropping point. The dropping point is the temperature at which a gel/paste/grease passes from a semi-solid to a liquid state under specific test conditions. It is commonly employed in the lubricants and grease industries. It is an indication of the type of thickener (gelator) used, and a measure of the cohesiveness of the fluid and gelator. The test is described in ASTM standards D-566 and D-2265. In general, the measurement is performed by using a small cup with a hole in the bottom, a block heater, and a thermometer. The gel is placed into the cup, and heated to the point at which it begins to flow through the hole at the bottom. General description taken from Wikipedia at http://en.wikipedia.org/wiki/Dropping point. Gel Dropping Point Data, provided in Table 1 below summarizes the dropping point results for TBPC and TPPC gelators in C$_6$ (hexane), C$_{12}$ (dodecane), and C$_{16}$ (hexadecane) hydrocarbon fluids at 1, 3, and 5 weight % gelator loadings. In general, we see a monotonic increase in dropping point with gelator concentrations.

TABLE 1

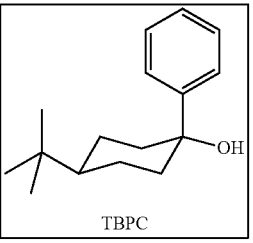

| gelator | fluid | % gelator | dropping point/° C. |
|---|---|---|---|
| TBPC | hexane (C$_6$) | 1% | No gel observed |
| | " | 3% | 40.5 |
| | " | 5% | 48.6 |
| | dodecane (C$_{12}$) | 1% | No gel observed |
| | " | 3% | 53.9 |
| | " | 5% | 59.8 |
| | hexadecane (C$_{16}$) | 1% | No gel observed |
| | " | 3% | 52.3 |
| | " | 5% | 56.5 |
| TPPC | hexane (C$_6$) | 1% | 46.1 |
| | " | 3% | 64.4 |
| | " | 5% | 79.4 |
| | dodecane (C$_{12}$) | 1% | 47.4 |
| | " | 3% | 58.8 |
| | " | 5% | 77.3 |
| | hexadecane (C$_{16}$) | 1% | 43.7 |
| | " | 3% | 65.3 |
| | " | 5% | 76 |

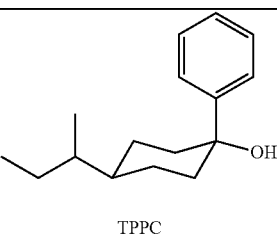

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A compound of the formula

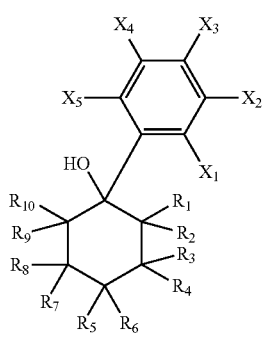

wherein R$_1$, R$_2$, R$_3$, R$_4$, R$_5$, R$_6$, R$_7$, R$_8$, R$_9$, and R$_{10}$ are each hydrogen and wherein X$_1$, X$_2$, X$_3$, X$_4$, and X$_5$ are each hydrogen;
and wherein the compound can optionally be a mixture of cis and trans isomers.

2. A compound comprising a cis and trans mixture of the formula

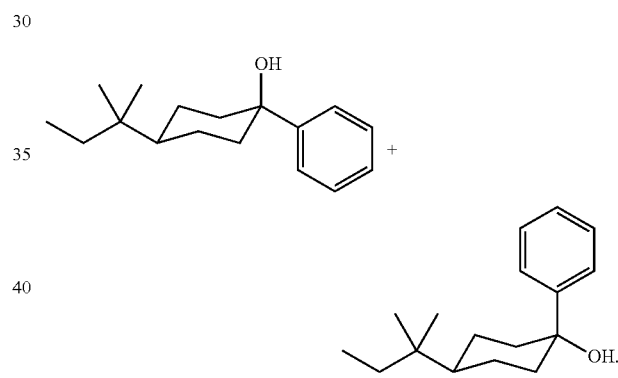

3. A composition comprising:
   a carrier; and
   a compound comprising a cis and trans mixture of the formula

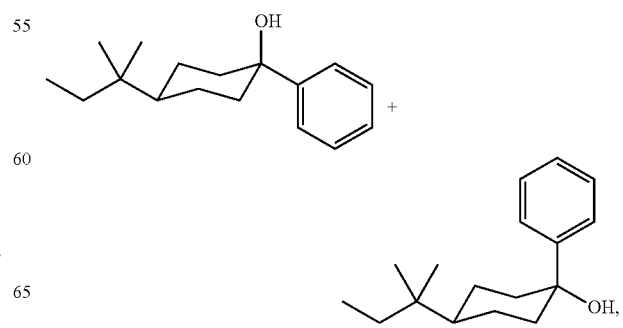

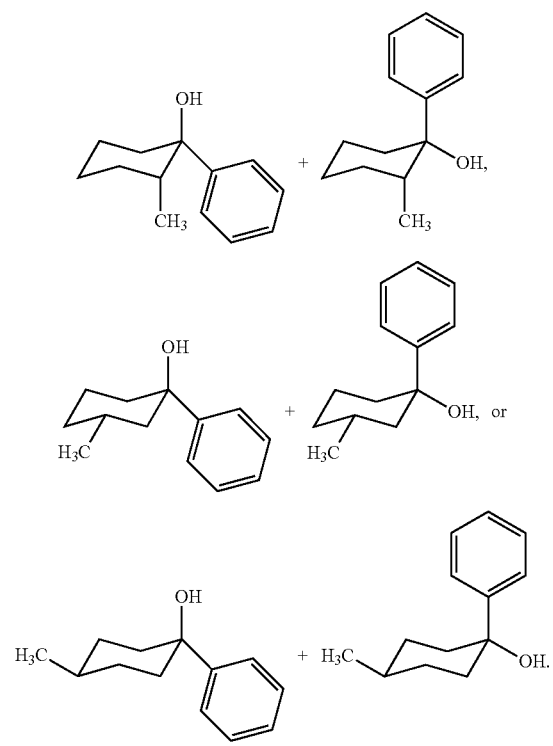

4. The composition of claim 3, wherein the carrier comprises a member of the group consisting of wax, oil, solvent, water, organic liquid, inorganic liquid, and combinations thereof.

5. A phase change ink comprising:
a carrier;
an optional colorant; and
a compound comprising a cis and trans mixture of the formula

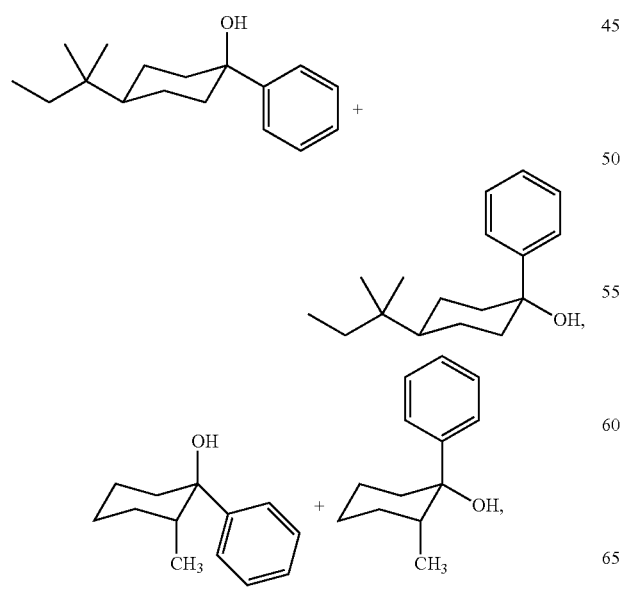

6. The phase change ink of claim 5, wherein the carrier comprises at least one wax.

7. The phase change ink of claim 5, wherein the carrier comprises at least one wax having a melting point of 120° C. or higher.

8. An ink jet printer stick or pellet containing a phase change ink composition comprising a carrier; an optional colorant; and a compound comprising a cis and trans mixture of the formula

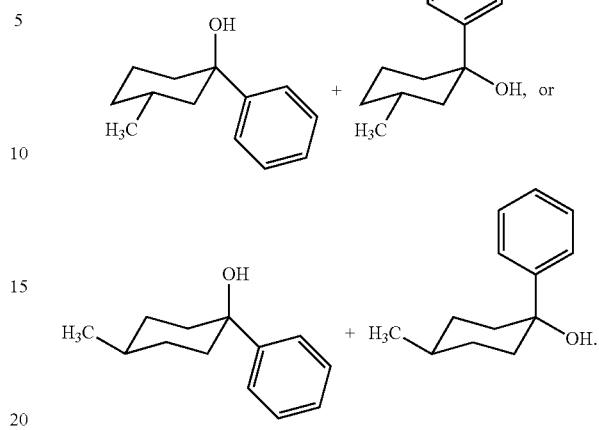

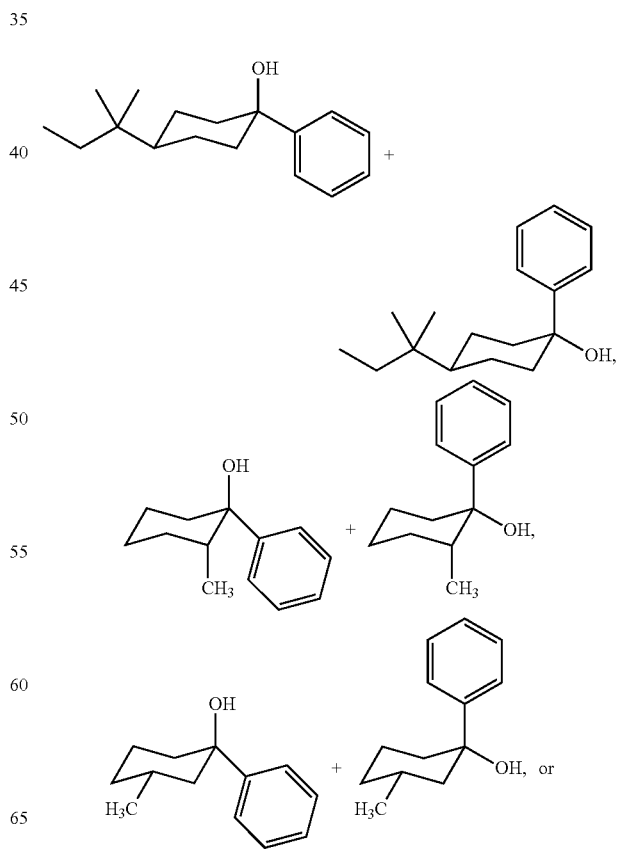

-continued
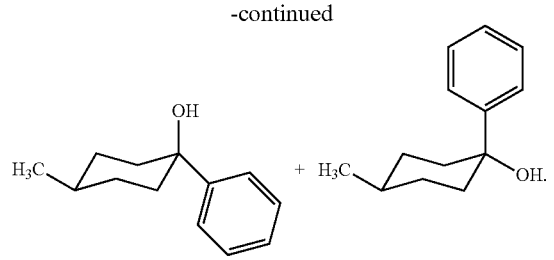
* * * * *